US00PP21318P3

(12) United States Plant Patent
Cline

(10) Patent No.: US PP21,318 P3
(45) Date of Patent: Sep. 28, 2010

(54) FOR A REDWOOD TREE NAMED 'RAVEN'

(50) Latin Name: *Metasequoia glyptostroboides*
Varietal Denomination: Raven

(75) Inventor: Steven Cline, St. Louis, MO (US)

(73) Assignee: Missouri Botanical Garden, St. Louis, MO (US)

( * ) Notice: Subject to any disclaimer, the term of this patent is extended or adjusted under 35 U.S.C. 154(b) by 0 days.

(21) Appl. No.: 12/151,573

(22) Filed: May 8, 2008

(65) Prior Publication Data

US 2009/0282591 P1 Nov. 12, 2009

(51) Int. Cl.
*A01H 5/00* (2006.01)

(52) U.S. Cl. ..... Plt./213

(58) Field of Classification Search ..... Plt./213
See application file for complete search history.

*Primary Examiner*—Annette H Para

(57) ABSTRACT

A new and distinct redwood tree named 'Raven', characterized by its uniformly symmetrical growth habit, low and uniform branching, deep furrowed and convoluted bark, beautiful disease-resistant, medium green thick foliage, and its outstanding vigor.

9 Drawing Sheets

Latin name of the genus and species of the plant claimed: *Metasequoia glyptostroboides*.

Variety denomination: 'Raven'.

BACKGROUND OF THE INVENTION

The present invention identifies *Metasequoia glyptostroboides* 'Raven' as a distinct cultivar in the family Taxodiaceae. The novel characteristics of this cultivar include an extremely uniform pyramidal form with a low branching habit, deeply furrowed, convoluted buttressed bark and fast growth rate. The convoluted bark gives this tree a distinctive "ancient" appearance. The 'Raven' redwood tree exhibits less variation in these characteristics that the common *Metasequoia glyptostroboides* and retains these desirable characteristics through asexual propagation.

The new cultivar 'Raven' was noted by Steven D. Cline growing in St. Louis, Mo. as a member of a group of seven redwood trees planted in 1952. The 'Raven' cultivar is unique amongst these seven trees being more uniformly pyramidal in habit at maturity (60 years) and displaying distinctive and attractive bark patterns with deep, netted convolutions that give this cultivar a notable ornamental appearance. In addition, the branching pattern of this cultivar is also distinctive; uniform from the lowest branch to the peak both in spiral distribution and vertical spacings around the trunk. These characteristics contrast with species and known cultivars of *Metasequoia glyptostroboides* whose branching patterns are more random, less uniform in spacing and with irregular outline from bottom to the top. The deeply fissured bark of 'Raven' is also notable in contrast to species and other cultivars becoming very distinctive in this regard extending from the base into the upper canopy to about 20 feet.

SUMMARY OF THE INVENTION

The present invention comprises a new and distinct cultivar of a redwood tree, botanically known as *Metasequoia glyptostroboides* and referred to by the cultivar name 'Raven'. This deciduous conifer tree is growing at 4344 Shaw Boulevard, St. Louis, Mo. (38°36'38.58"N, 90°15'30.50"W).

*Metasequoia* is an ancient genus dating back to the Lower Pliocene. Living specimens of this fossil genus were discovered in Central China in 1941. In 1944, specimens were collected, and in 1945 they were found to belong to a conifer genus previously unknown in the living flora of China. On later expeditions, seeds were collected and distributed to several universities, botanical gardens and arboreta, including Missouri Botanical Garden. By 1948, many had germinated, and in 1952, seven trees were moved to their present location on the east side of the John S. Lehmann building. 'Raven' is an exceptional specimen from this grove of trees.

The 'Raven' cultivar is a unique form of *Metasequoia glyptostroboides* whose growth habit is extremely uniformly pyramidal (FIG. 2) with a low, uniform branching habit (FIG. 3) and deeply furrowed, convoluted bark (FIG. 4). This convoluted bark gives the tree a very distinctive and "ancient" appearance. The 'Raven' dawn redwood has few disease and pest problems. It exhibits a medium to fast growth rate; up to 3 feet each year for established trees. Being a deciduous conifer, the 'Raven' dawn redwood has very light/fine foliage that presents very little effort in regard to fall clean up. Therefore, it is not considered a messy tree that would otherwise present maintenance issues for a home landscape. It tolerates both wet and dry soils. It is hardy to Zone 4 (USDA Hardiness Zone Map).

As an ornamental specimen, the cultivar 'Raven' would be considered unique for the ornamental market both in terms of distinctive form as well as rapid growth rate without wood weakness. Presently, few larger trees for the ornamental landscape in today's market provide both pyramidal shape for use in narrow locations, deciduous foliar character for drought tolerance in winter, and tolerance to both dry and wet soil conditions. The cultivar 'Raven' has been easily propagated from both softwood and hardwood scion cuttings taken from random areas of the mother tree and successfully rooted. The speed of propagation and fast growth rate exceeding three feet per year are characteristics which will allow this plant to be marketed widely.

The new 'Raven' cultivar has been successfully asexually propagated by rooted hardwood and softwood cuttings taken from various branch locations on the mother tree. Cuttings (8–10 inches long×¼ inch diameter) were treated with rooting hormone and placed under mist. These cuttings were planted in 2004 and have produced 6–7 foot trees with a 2–3 foot spread by 2007 (FIG. 9). These clones are identical to the original plant in all distinguishing characteristics.

*Metasequoia glyptostroboides* 'Raven' exhibits the following characteristics, which in combination, distinguish this cultivar selection from other specimens of *Metasequoia glyptostroboides:*

1. The 'Raven' dawn redwood tree has an extremely uniform pyramidal growth habit.
2. The 'Raven' dawn redwood has a low branching habit with branches uniformly spaced.
3. The 'Raven' dawn redwood has deeply furrowed bark, giving the tree a very "ancient" appearance.
4. Foliage of 'Raven' has few foliar disease problems and is therefore resistant to disease.
5. The 'Raven' dawn redwood exhibits remarkable vigor. Once established, the 'Raven' dawn redwood grows up to 3 feet each year.

BRIEF DESCRIPTION OF THE DRAWINGS

The accompanying colored photographs illustrate the appearance and color of the 'Raven' dawn redwood tree. These photographs show the color as accurately as is reasonably possible to obtain in colored reproductions of this type. Actual foliage colors may differ slightly due to light reflectance.

DETAILED BOTANICAL DESCRIPTION OF THE PLANT

Figure 1:
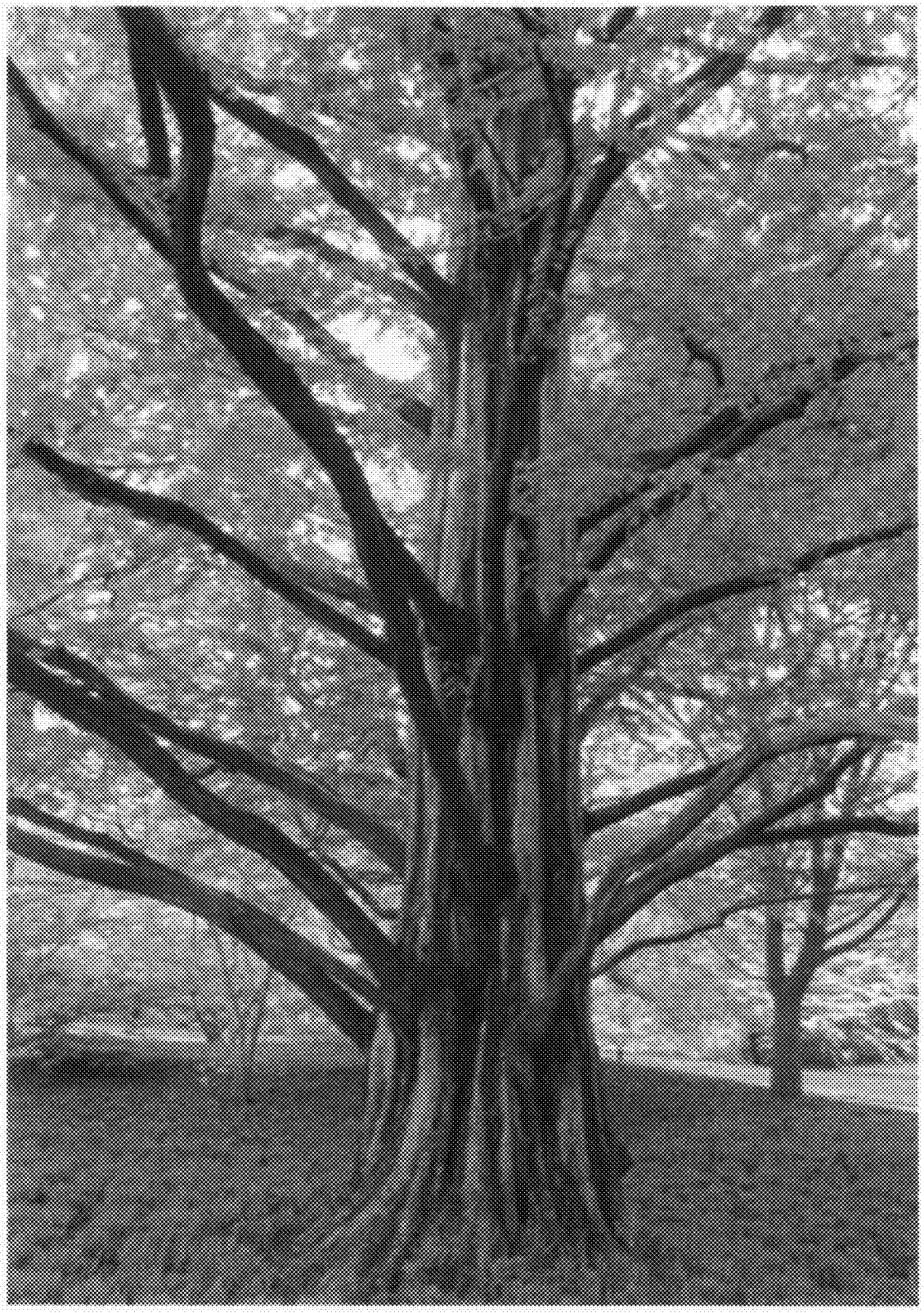
FIG. 1 depicts the 'Raven' dawn redwood tree in spring foliage.
Figure 2:
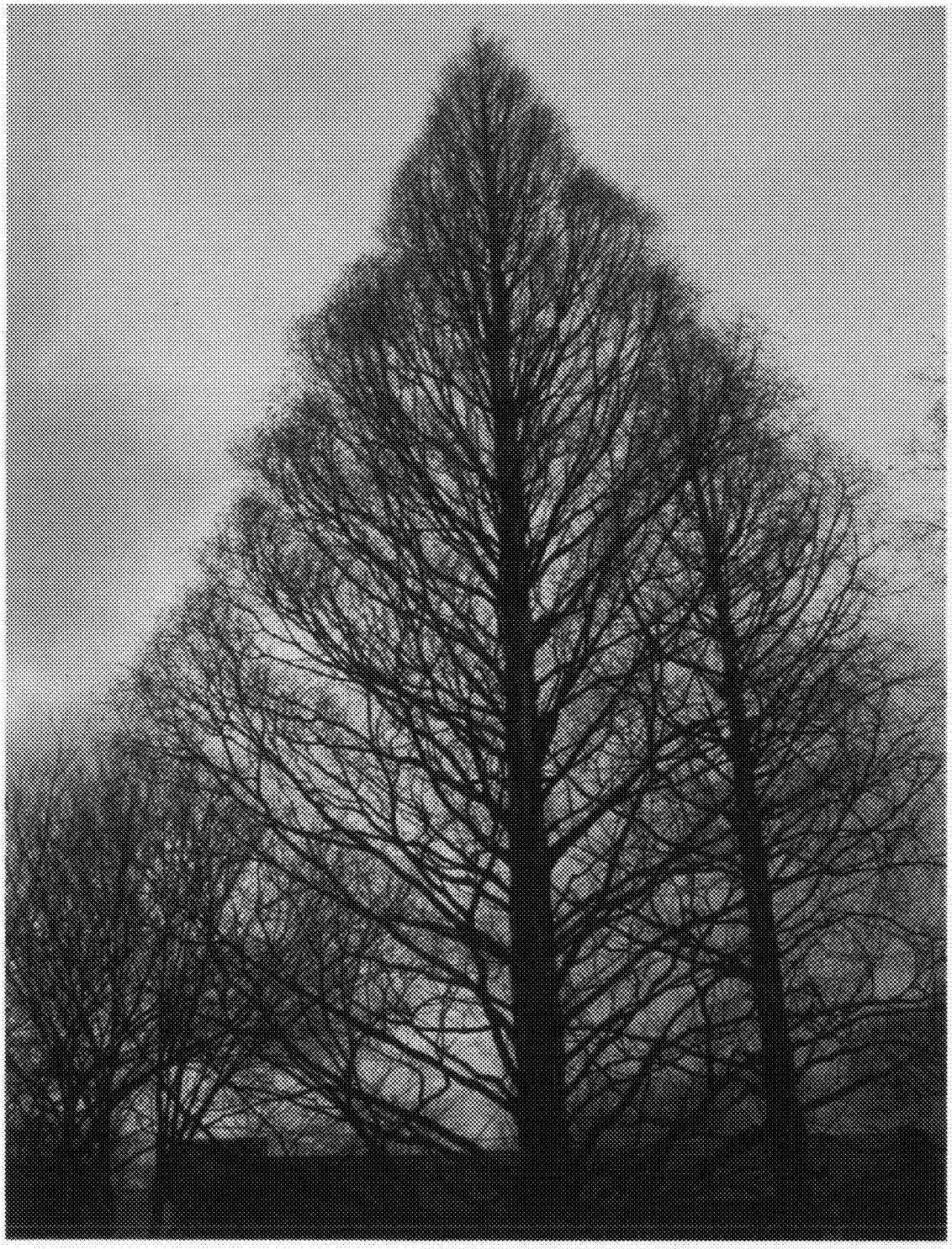
FIG. 2 depicts the 'Raven' dawn redwood tree in winter foliage and the extremely pyramidal growth form and uniformly spaced branches.
Figure 3:
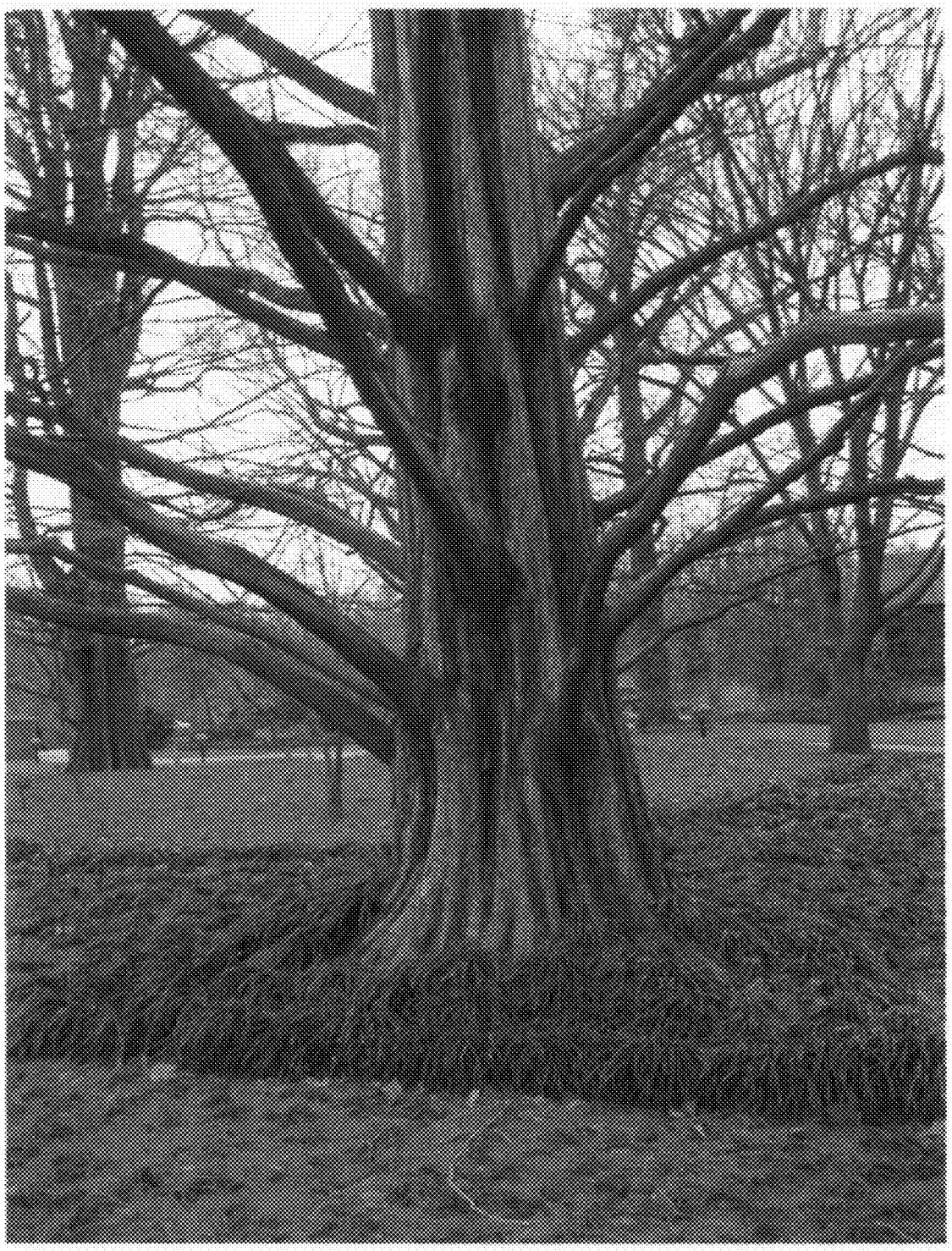
FIG. 3 depicts the low, uniform branching habit and the deeply furrowed and fluted trunk of the 'Raven' dawn redwood.
Figure 4:
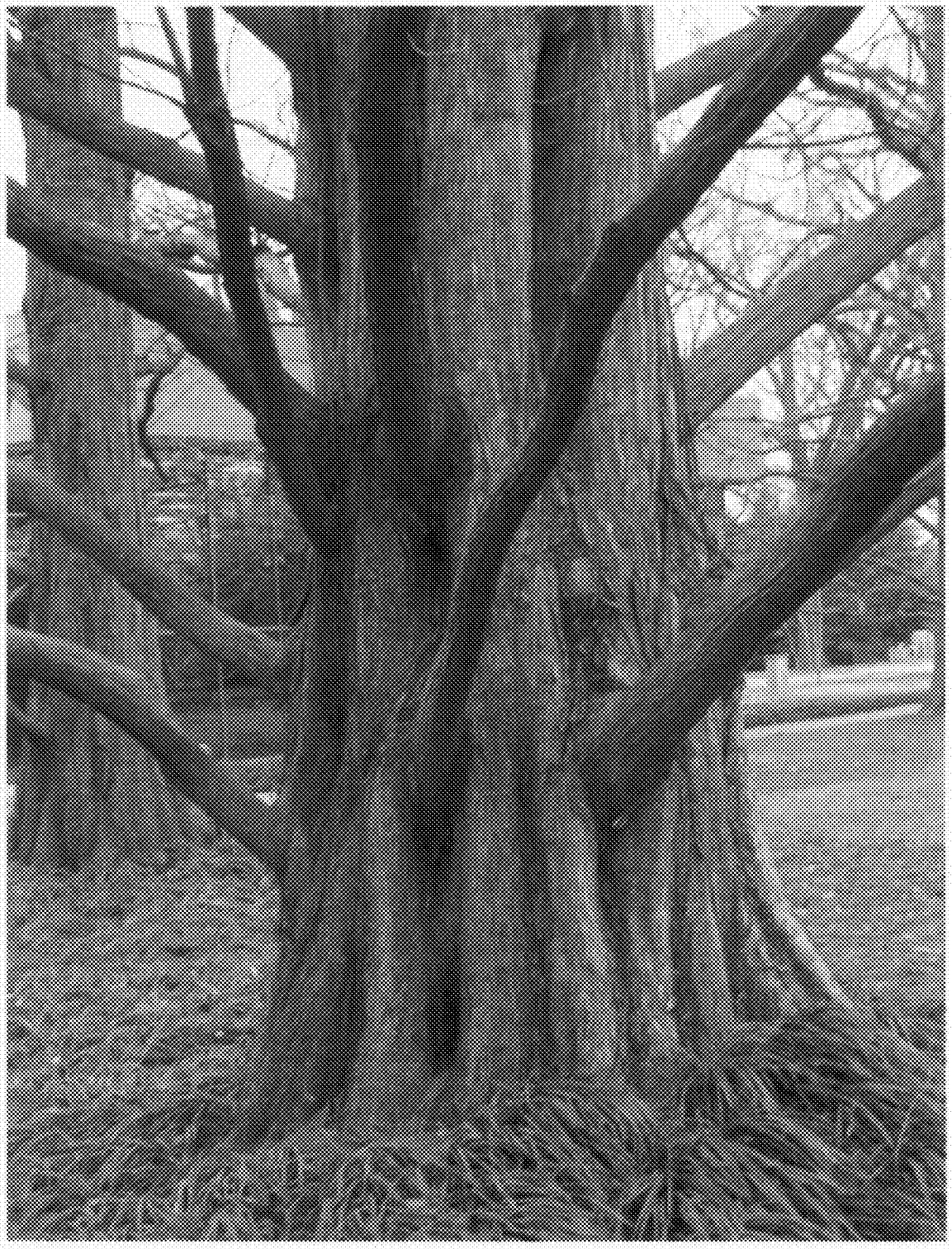
FIG. 4 is a closer image of branching habit, and the deeply furrowed and fluted trunk near the base of the 'Raven' dawn redwood.
Figure 5:
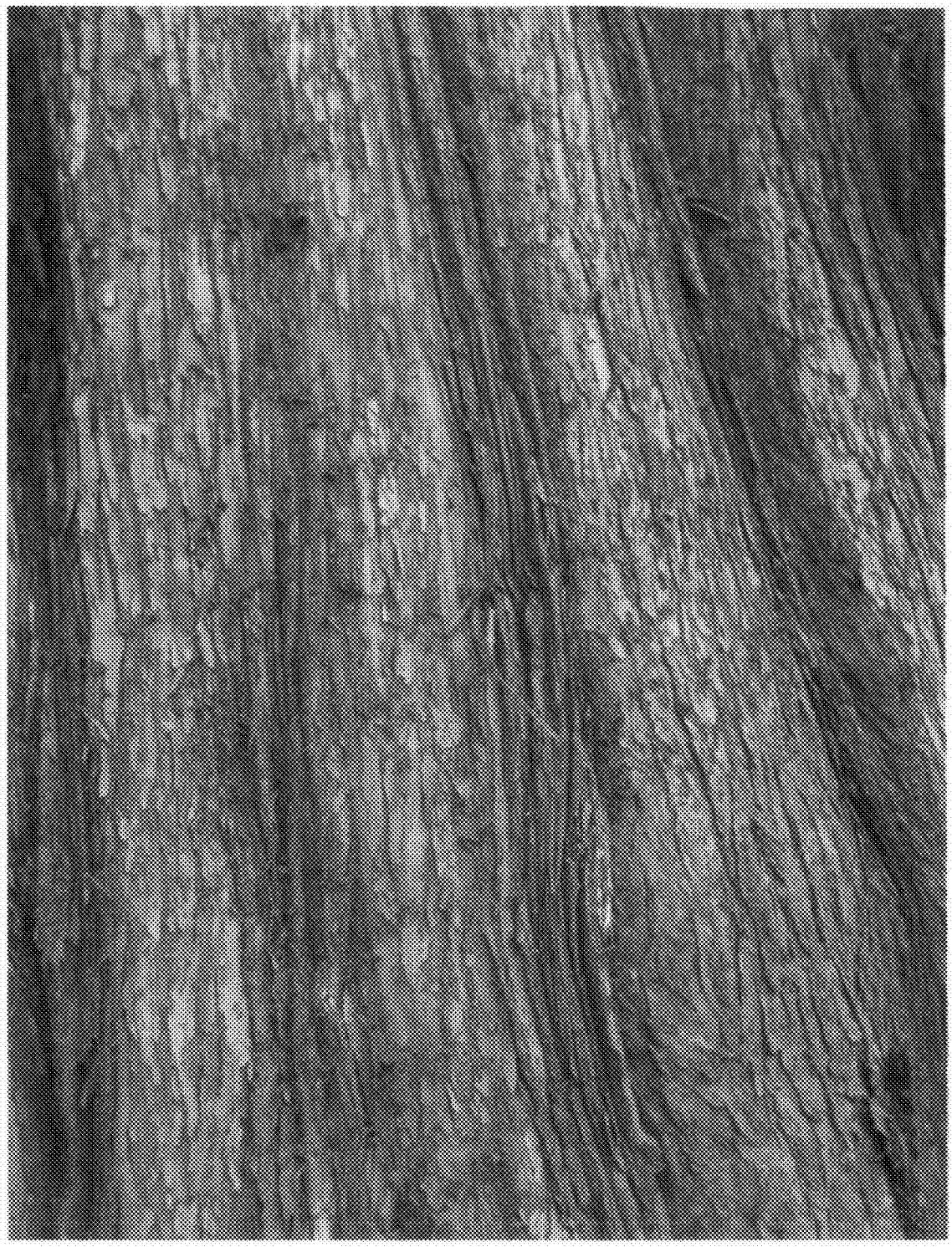
FIG. 5 is a close-up of the bark of the 'Raven' dawn redwood.
Figure 6:
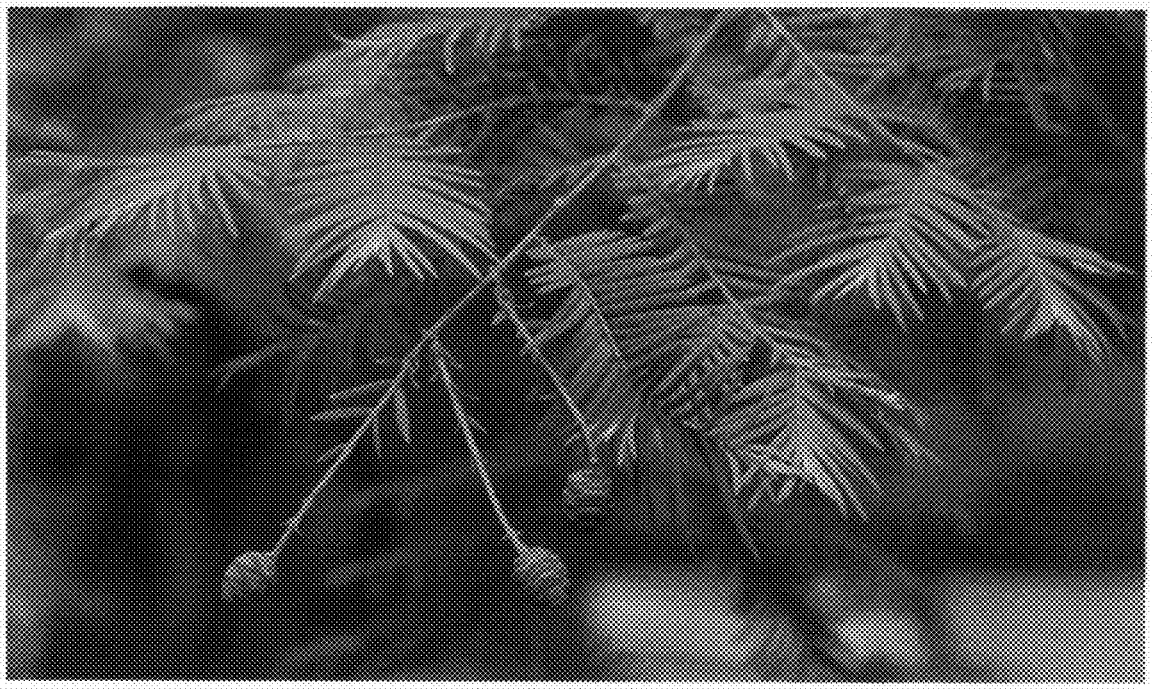
FIG. 6 depicts the stem, leaves, and immature female cones.
Figure 7:
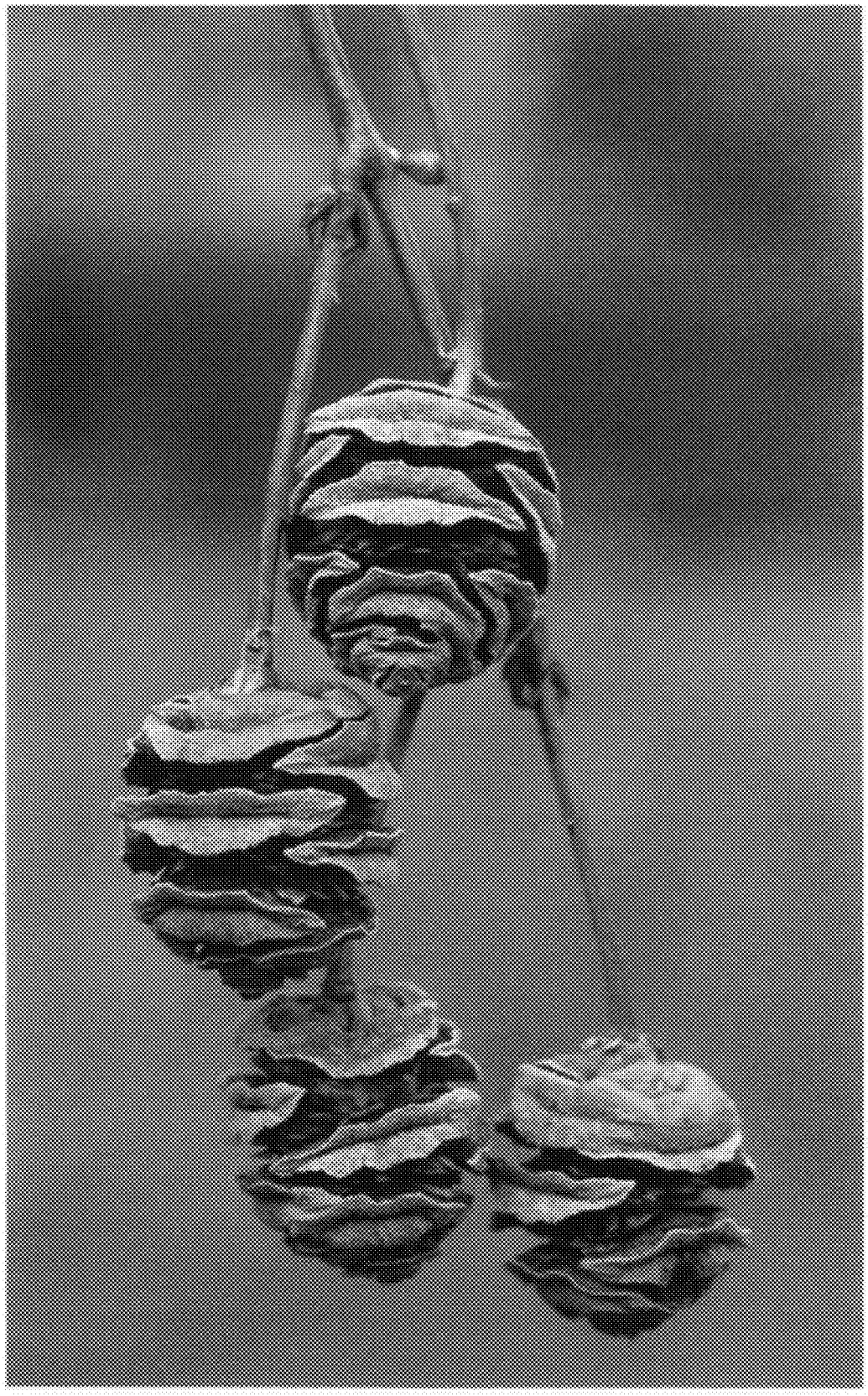
FIG. 7 depicts the mature female cones.
Figure 8:
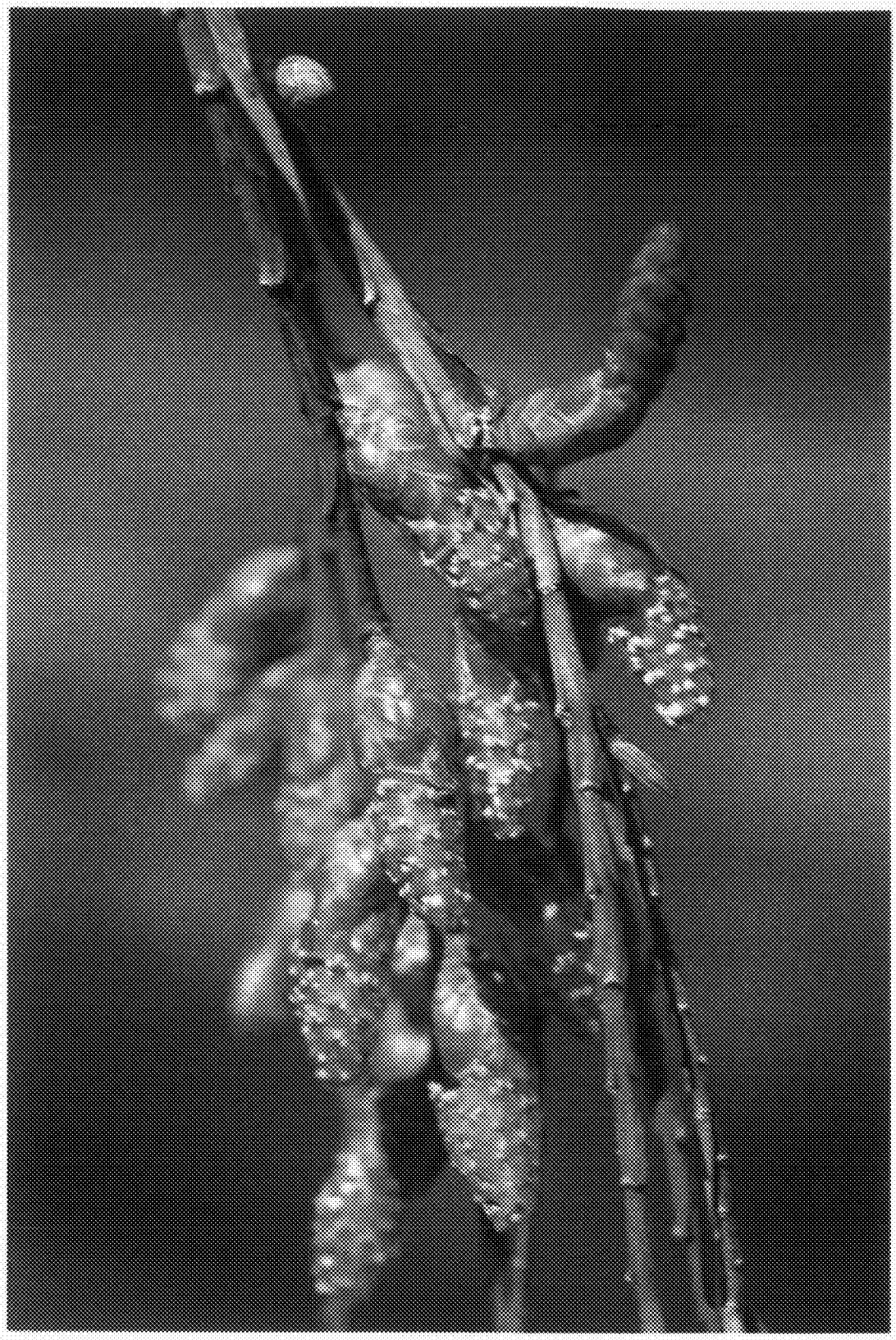
FIG. 8 depicts the mature male cones.
Figure 9:
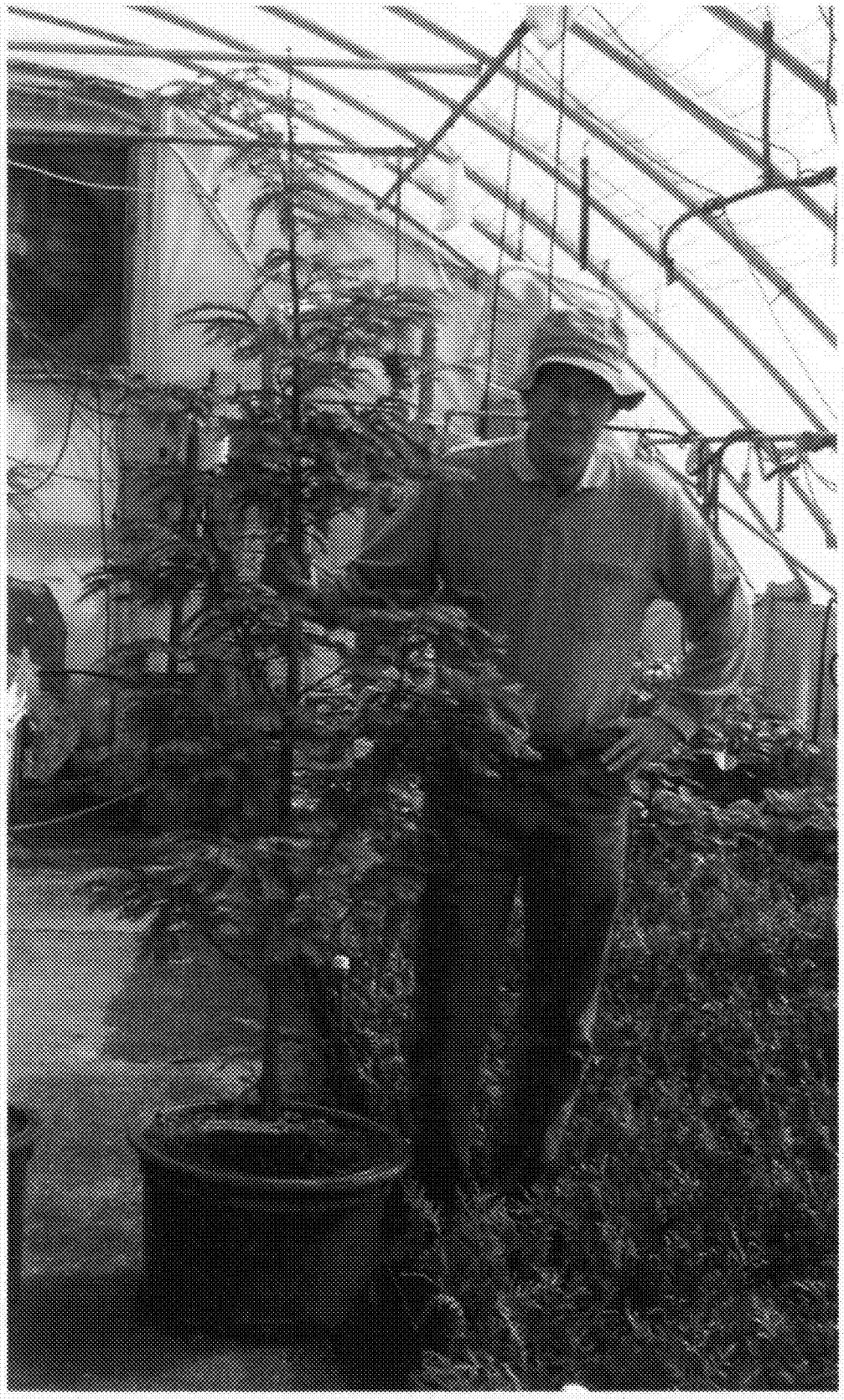
FIG. 9 asexually scion-cutting propagated tree comes true to form.

In the following description, color references are made to The Royal Horticultural Society Colour Chart.

Name: *Metasequoia glyptostroboides* 'Raven'.

Market class: Deciduous conifer tree.

Parentage: Species.

Classification: *Metasequoia glyptostroboides* 'Raven'.

Where discovered: In a cultivated area on the grounds of Missouri Botanical Garden, 4344 Shaw Blvd, St. Louis, Mo. 63110.

This plant has been asexually reproduced from: Rooted hardwood and softwood ¼" diameter scion cuttings taken from branches of the mother plant.

Present propagation is being done: Albers, Ill.; Elsberry, Mo.; St. Louis, Mo.

Form: Tree.

Shape: Pyramidal.

Height: 29 meters (95 feet).

Spread: 15 meters (50 feet).

Age: 59 years.

Trunk size: 1.06 meters (42 inches).

Base: Buttressed, to 2.5 m d.b.h.

Bark: Of young trees pale orange-brown with darker flakes and exfoliating, finally dark reddish brown (RHS 167A) to gray (RHS 197A), fissured.

Growth rate: Fast.

Strength: Excellent.

Branches:

*Angle of attachment.*—Branches ascending, 30° (lower portion) — 45° (middle portion) — 60° (upper portion), branchlets pendulous.

*Spacing.*—More dense at upper portion relative to lower portion.

*Bark.*—Of young trees pale orange-brown with darker flakes and exfoliating, finally dark reddish-brown (RHS 167A) to gray (RHS 197A).

Stem (non-deciduous branchlet):

*Outer surface.*—Axis pinkish green or pale purple in first year, later brownish gray color (165A), smooth in texture; scale-like leaf occurs spiraled around the branchlet; lateral branchlets deciduous, opposite, each subtended by leaflike scale.

*Lenticels.*—None.

*Buds.*—Winter buds to 5×3 mm, apex obtuse, scales light reddish or yellowish brown (165B), ca. 2–2.5×2–2.5 mm (μ=2.25×2.25 mm).

Leaves (deciduous branchlet, lateral branchlet): Lateral branchlets with longer and shorter leaves alternating irregularly, forming an ovate-elliptic outline 3–7×1.5–4 cm (μ=5×2.75 cm). Leaves borne at 45–60° to branchlet axis, 2–5 mm (μ=3.5 mm) apart.

*Length.*—3–7 cm (μ=5 cm).

*Color.*—Bluish green or yellowish green adaxially (144B), paler abaxially, turning orange or red in autumn.

*Texture* (*smooth, rought, warty, etc.*).—smooth.

Lamina:

*Length.*—0.8–1.5 cm (μ=1.0 cm) on old trees but longer on younger trees.

*Width.*—1.2–2 mm (μ=1.75 mm).

*Form.*—Linear, flattened, pectinately arranged 2–5 mm (μ=3.5 mm) apart, apex obtuse or with hyaline mucro, more sharply acute on leaves of leader branchlets.

*Margin.*—Smooth.

*Texture.*—Upper surface smooth with narrowly grooved midvein, lower surface bearing obscure lines of stomata, slightly glaucous.

*Quantity.*—50–60 (μ=55) per branchlet, abundant.

*Color.*—Bluish green or yellowish green adaxially, paler abaxially, turning orange or red in autumn (144B).

*Ribs and veins.*—Marginal bands 0.5–0.6 mm (μ=0.55 mm) wide, narrowly grooved midvein, the midrib slightly raised.

Pollen cones: Monoecious; male pollen cones ovoid 2.5–5.5×2–3.8 mm (μ=4×2.9 mm), numerous, decussately arranged on racemes or panicles; bracts triangular-ovate or obovate, ca. 4×3 mm, lowest minutely ciliate distally, others glabrous (145A).

Seed cones: Female seed cones solitary, purplish black when young, oblong-ellipsoid and to 9×5.5 mm at pollination, subglobose and 1.4–2.5×1.6–2.3 cm (μ=1.95×1.95 cm) when mature; solitary and pendulous on long stalks of sparsely leaved lateral branchlets; basal cone scales 9-ovulate, middle 7-ovulate, distal 5-ovulate, apical sterile; the outer surface of the scale transversely elliptic or broadly triangular, with a horizontal groove; seeds light brown (164A), usually obovate, ca. 5×4 mm, with 2 broad, thin, paler wings; cotyledons usually 2; pollination February–March, before leaves, seed maturity October–November.

Has this plant ever been offered for sale?: No.

Claim:

1. A new and distinct cultivar of a redwood tree, *Metasequoia glyptostroboides,* named 'Raven', as illustrated and described.

* * * * *